(12) United States Patent
Park et al.

(10) Patent No.: US 10,433,836 B2
(45) Date of Patent: Oct. 8, 2019

(54) SUTURING DEVICE FOR SURGERY

(71) Applicant: NATIONAL CANCER CENTER, Goyang-Si, Gyeonggi-do (KR)

(72) Inventors: Sang Jae Park, Goyang-Si (KR); Kwang Gi Kim, Goyang-Si (KR); Seong Yeon Cho, Goyang-Si (KR); Sung Ho Cho, Goyang-Si (KR)

(73) Assignee: NATIONAL CANCER CENTER, Goyang-Si (KR)

( * ) Notice: Subject to any disclaimer, the term of this patent is extended or adjusted under 35 U.S.C. 154(b) by 277 days.

(21) Appl. No.: 15/310,678

(22) PCT Filed: May 14, 2015

(86) PCT No.: PCT/KR2015/004834
§ 371 (c)(1),
(2) Date: Nov. 11, 2016

(87) PCT Pub. No.: WO2015/174752
PCT Pub. Date: Nov. 19, 2015

(65) Prior Publication Data
US 2017/0071601 A1 Mar. 16, 2017

(30) Foreign Application Priority Data
May 14, 2014 (KR) ........................ 10-2014-0057829

(51) Int. Cl.
*A61B 17/12* (2006.01)
*A61B 17/062* (2006.01)
(Continued)

(52) U.S. Cl.
CPC ........ *A61B 17/062* (2013.01); *A61B 17/0469* (2013.01); *A61B 17/0491* (2013.01); *A61B 17/0625* (2013.01); *A61B 17/29* (2013.01)

(58) Field of Classification Search
CPC ... A61B 17/04; A61B 17/062; A61B 17/0491; A61B 17/0469; A61B 17/12
See application file for complete search history.

(56) References Cited

U.S. PATENT DOCUMENTS

| 5,480,406 A | 1/1996 | Nolan et al. |
| 5,728,107 A | 3/1998 | Zlock et al. |

(Continued)

FOREIGN PATENT DOCUMENTS

| JP | 3792687 B2 | 7/2006 |
| JP | 2009-279395 A | 12/2009 |

(Continued)

*Primary Examiner* — Vi X Nguyen
(74) *Attorney, Agent, or Firm* — McCarter & English, LLP; David R. Burns

(57) ABSTRACT

A suturing device for surgery according to the present invention includes: a body unit; a pair of suturing operation units which are supported by a frontal end of the body unit and are rotated between a first mode, in which the pair of suturing operation units are tooth-engaged to each other with a suture area therebetween so that a suturing needle supported by any one of the pair of suturing operation units penetrates through the suture area and is transferred to the other suturing operation unit, and a second mode, in which the suturing needle supported by the other suturing operation unit in the first mode is transferred to any one of the pair of suturing operation units; and a driving unit for providing a driving force to at least one of the pair of suturing operation units so that the pair of suturing operation units are rotated between the first mode and the second mode.

16 Claims, 16 Drawing Sheets

(51) Int. Cl.
*A61B 17/04* (2006.01)
*A61B 17/29* (2006.01)

(56) References Cited

U.S. PATENT DOCUMENTS

| | | | |
|---|---|---|---|
| 7,879,046 B2 * | 2/2011 | Weinert | A61B 17/0469 606/139 |
| 8,057,489 B2 | 11/2011 | Stone et al. | |
| 2009/0259233 A1 | 10/2009 | Bogart et al. | |

FOREIGN PATENT DOCUMENTS

| | | |
|---|---|---|
| KR | 101176324 B1 | 8/2012 |
| WO | 2011052872 A1 | 5/2011 |

\* cited by examiner

SUTURING DEVICE FOR SURGERY

RELATED APPLICATION

This application is a national stage filing under 35 U.S.C. § 371 of International Application No. PCT/KR2015/004834 filed on May 14, 2015, which claims priority under 35 U.S.C. § 365 to Korean Patent Application No. 10-2014-0057829 filed on May 14, 2014. The entire contents of each of the aforementioned applications are incorporated herein by reference.

TECHNICAL FIELD

The present invention relates to a suturing device for surgery, and more particularly, to a suturing device for surgery to suture an area on which laparotomy and laparoscopic surgery is performed.

BACKGROUND ART

Generally, suturing needle and thread are used to suture a patient's body tissue cut during laparotomy and laparoscopic surgery, in which the suturing needle has a curved shape for efficient suturing.

Here, the suture needle may be held by an operator's hand or mounted in a suturing device for use in suturing. Such suturing directly performed by an operator not only requires professional competence but also increases an operator's fatigue.

In laparoscopic surgery, a plurality of trocars are inserted into the abdomen of a patient, and the patient's abdomen is insufflated with gas, such as carbon dioxide, which provides air in the peritoneal cavity to secure space for laparoscopic surgery. In the laparoscopic surgery, an endoscope and various medical instruments are inserted through the trocars so that laparoscopic surgery may be performed on a diseased area. As an example thereof, Korean Patent No. 10-1176324 discloses a "suture apparatus for laparoscopic surgery."

However, in a suture procedure for suturing a narrow affected part such as in laparoscopic surgery, the area is difficult to be directly sutured by an operator, and the body tissue may also be damaged, such that a suturing device was introduced, in which a suturing needle is mounted for use in suturing.

DISCLOSURE

Technical Problem

An object of the present invention is to provide a suturing device for surgery with improved structure, in which suturing may be performed continuously in minimally invasive surgery such as laparoscopic surgery.

Technical Solution

In order to achieve the above object, the present invention provides a suturing device for surgery, the device including: a body unit; and a pair of suturing operation units, which are supported at a front end of the body unit and rotates between a first mode, in which the pair of suturing operation units are tooth-engaged with each other with a suture area therebetween so that a suturing needle held by any one of the pair of suturing operation units passes through the suture area and is transferred to the other one of the pair of suturing operation units, and a second mode, in which the suturing needle held by the other one of the pair of suturing operation units in the first mode is transferred to any one of the pair of suturing operation units; and a driving unit configured to provide a driving force to at least any one of the pair of suturing operation units so that the pair of suturing operation units rotate between the first mode and the second mode.

Here, the suturing device for surgery may further include a suturing needle pushing unit configured to apply pressure to the suturing needle in the first mode, so that the suturing needle, supported by any one of the pair of suturing operation units, is transferred to the other one of the pair of suturing operation units to be held thereby.

The suturing needle pushing unit may preferably have a through-hole, through which a suturing thread, threaded through the suturing needle, passes.

The pair of suturing operation units may include: a suturing needle holder unit, which is supported at the front end of the body unit, and is configured to hold the suturing needle transferred after passing through the suture area in the first mode; and a suturing needle grip unit, which is engaged with or disengaged from the suturing needle holder unit, and is configured to transfer the suturing needle gripped in the first mode to the suturing needle holder unit, and to grip the suturing needle held by the suturing needle holder unit in the second mode.

The suturing needle holder unit may be preferably fixed to the front end of the body unit, and may include a receiving hole into which the suturing needle is inserted.

Further, the suturing needle grip unit may reciprocally rotate to be engaged with and disengaged from the suturing needle holder unit, wherein the suturing needle grip unit may be preferably engaged with the suturing needle holder unit with the suture area therebetween in the first mode, and may be preferably engaged directly with the suturing needle holder unit in the second mode.

The suturing needle grip unit may include a grip body, which reciprocally rotates with respect to the suturing needle holder unit, and is engaged with and disengaged from the suturing needle holder unit; and a grip unit, which is releasably connected to the grip body to correspond to the receiving hole of the suturing needle holder unit and to a cross-sectional area of the suturing needle.

In addition, the pair of suturing operation units may further include an elastic supporting unit, which is interposed between the grip body and the grip unit or is disposed on an upper portion of the grip unit, to elastically grip the suturing needle.

Each of the suturing needle holder unit and the suturing needle grip unit may be preferably provided with an engaging unit, which is engaged with respect to the suture area in the first mode to support the suture area.

Further, the suturing device for surgery may further include a locking unit, which is disposed at any one of the pair of the suturing operation units, the one being positioned at a downstream side in an insertion direction of the suturing needle, and is configured to lock and unlock the suturing needle between the first mode and the second mode.

The suturing needle may have a latch groove, and the locking unit may include: a first locking unit, which is disposed at a lower portion of the suturing needle holder unit, and reciprocates in a direction transverse to the insertion direction of the suturing needle, so as to be locked into and unlocked from the latch groove of the suturing needle; and a second locking unit, which is disposed at one side of the first locking unit, and is lifted up and down by rotation of the suturing needle grip unit, to enable the first locking unit to reciprocate between a locking position and an unlocking position of the suturing needle.

The one side of the first locking unit may preferably come into contact with the second locking unit with any one of a tapered shape or a round shape, and as the second locking unit lifts up and down, the first locking unit may reciprocate in a direction transverse to the up-and-down direction of the second locking unit.

Further, the locking unit may further include a movement limiting unit, which is positioned adjacent to the other side of the first locking unit, which faces the one side of the first locking unit, to limit movement of the first locking unit.

In addition, the suturing device for surgery may further include an elastic member, which is disposed at a lower portion of the second locking unit to elastically bias the second locking unit.

The driving unit may include: a first driving unit configured to provide a driving force to at least any one of the pair of suturing operation units; and a second driving unit configured to provide a rotational driving force to the suturing needle pushing unit.

In order to achieve the above object, the present invention also provides a suturing device for surgery, the device including: a body unit; and a suturing operation unit, which includes a suturing needle holder unit that is supported at a front end of the body unit, and a suturing needle grip unit that rotates relative to the suturing needle holder unit, and which is configured to reciprocate between a first mode in which the suturing needle holder unit and the suturing needle grip unit are tooth-engaged with each other with a suture area therebetween so that a suturing needle gripped by the suturing needle grip unit passes through the suture area and is transferred to the suturing needle holder unit, and a second mode in which the suturing needle held by the suturing needle holder unit in the first mode is transferred to the suturing needle grip unit; a suturing needle pushing unit configured to apply pressure to the suturing needle in the first mode, to transfer the suturing needle to the suturing needle holder unit; and a driving unit comprising a first driving unit configured to provide a driving force to enable the suturing needle grip unit to rotate relative to the suturing needle holder unit, and a second driving unit positioned adjacent to the first driving unit and configured to provide a rotational driving force to the suturing needle pushing unit to enable the suturing needle to be held by the suturing needle holder unit in the first mode.

Here, the suturing needle may have a latch groove; and the suturing device for surgery may further include a locking unit, which is disposed at a lower portion of the suturing needle holder unit, and is locked into the latch groove in the first mode and is unlocked from the latch groove in the second mode.

Details of other exemplary embodiments are included in the detailed description and the drawings.

Advantageous Effects

The advantageous effects of the suturing device for surgery according to the present invention are as follows.

First, a pair of suturing operation units, which hold and grip a suturing needle, are provided so that suturing may be performed continuously by repeating a process of transferring a suturing needle from any one suturing operation unit to the other suturing operation unit, thereby improving efficiency in the suturing procedure.

Second, suturing is performed by repeating a process of transferring a suturing needle from any one suturing operation unit to the other suturing operation unit, such that a suturing procedure may be performed in a simple manner, thereby reducing an operator's fatigue.

BEST MODE

Figure 1:
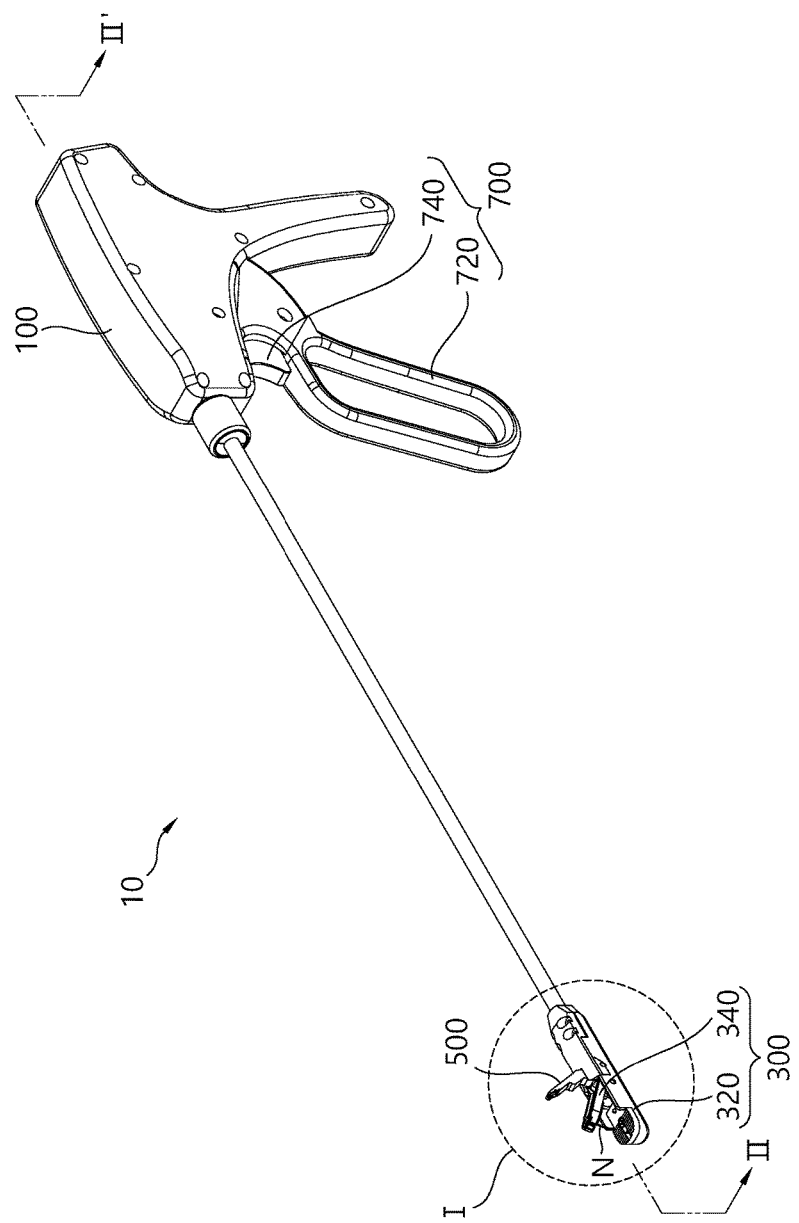
FIG. 1 is a perspective view of a suturing device for surgery according to an exemplary embodiment of the present invention.

Hereinafter, the suturing device for surgery according to exemplary embodiments of the present invention will be described in detail with reference to the accompanying drawings.

Before describing the present invention, it is to be understood that the suturing needle used in the suturing device for surgery according to the exemplary embodiments of the present invention is illustrated in the drawings, but the suturing thread, threaded through a suturing needle, is not illustrated therein.

Figure 2:
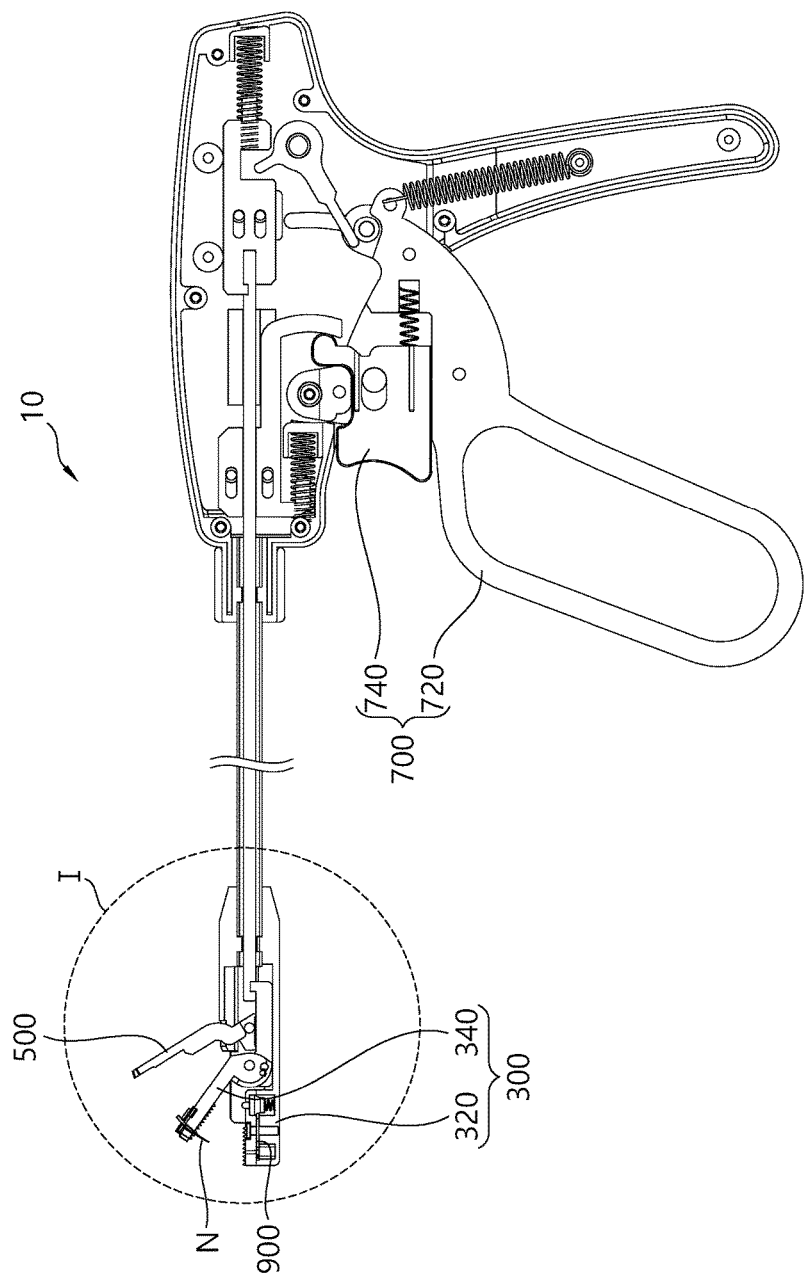
FIG. 2 is a cross-sectional view thereof taken along line II-II of FIG. 1.
Figure 3:
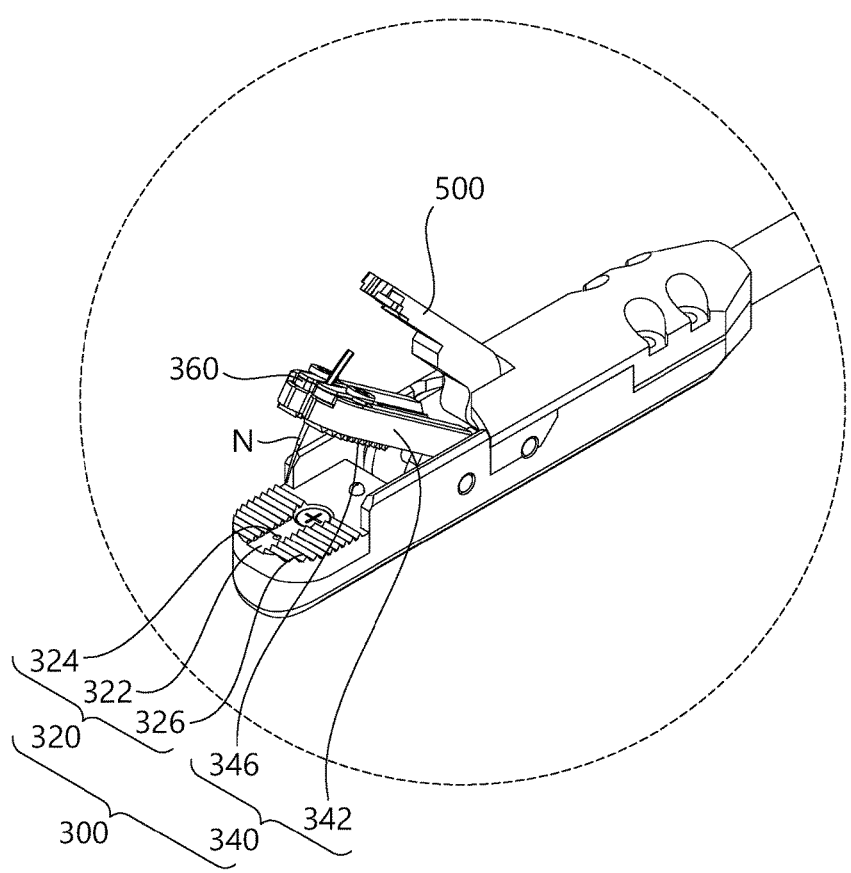
FIG. 3 is an enlarged view of area "I" illustrated in FIGS. 1 and 2.

FIG. 1 is a perspective view of a suturing device for surgery according to an exemplary embodiment of the present invention; FIG. 2 is a cross-sectional view thereof taken along line II-II of FIG. 1; FIG. 3 is an enlarged view of area "I" illustrated in FIGS. 1 and 2; and FIG. 4 is a cross-sectional view of the suturing device for surgery illustrated in FIG. 3.

As illustrated in FIGS. 1 to 4, the suturing device 10 for surgery according to the exemplary embodiments of the present invention includes a body unit 100, a suturing operation unit 300, a suturing needle pushing unit 500, a driving unit 700, and a locking unit 900. The suturing device 10 for surgery according to the exemplary embodiments of the present invention is mainly used for suturing a narrow suture area, such as a suture area in laparoscopic surgery. Here, a suturing needle (N) used in the suturing device for surgery according to the present invention includes a latch groove (L) (see FIGS. 13 to 16) which is locked or unlocked by the locking unit 900. Such latch groove (L) is not limited to the shape illustrated in the drawings of the present invention, and the shape may be changed.

The body unit 100 has a shape of a tube that connects an area, where the driving unit 700 is disposed, with the suturing operation unit 300 and the needle pushing unit 500. The shape of the body unit 100 may vary depending on changes in the design of the suturing device 10 for surgery according to the embodiments of the present invention.

Figure 4:
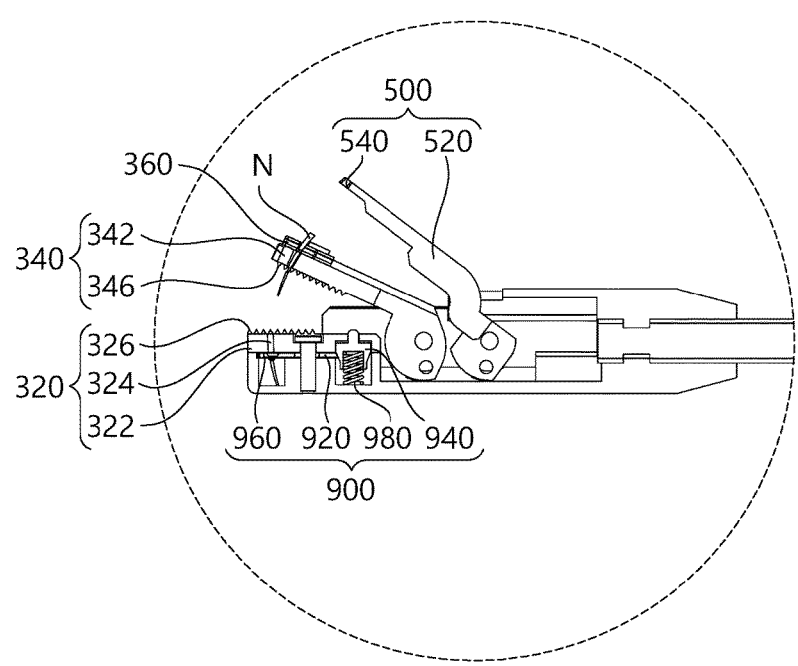
FIG. 4 is a cross-sectional view of the suturing device for surgery illustrated in FIG. 3.
Figure 5:
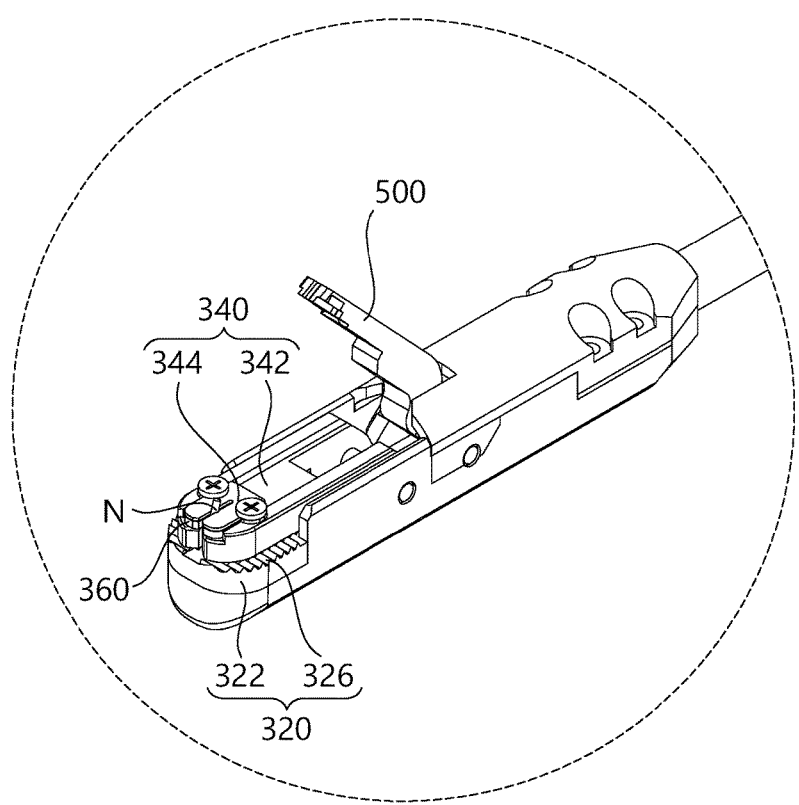
FIG. 5 is a first operational perspective view of a first mode of the suturing device for surgery illustrated in FIG. 4.
Figure 6:
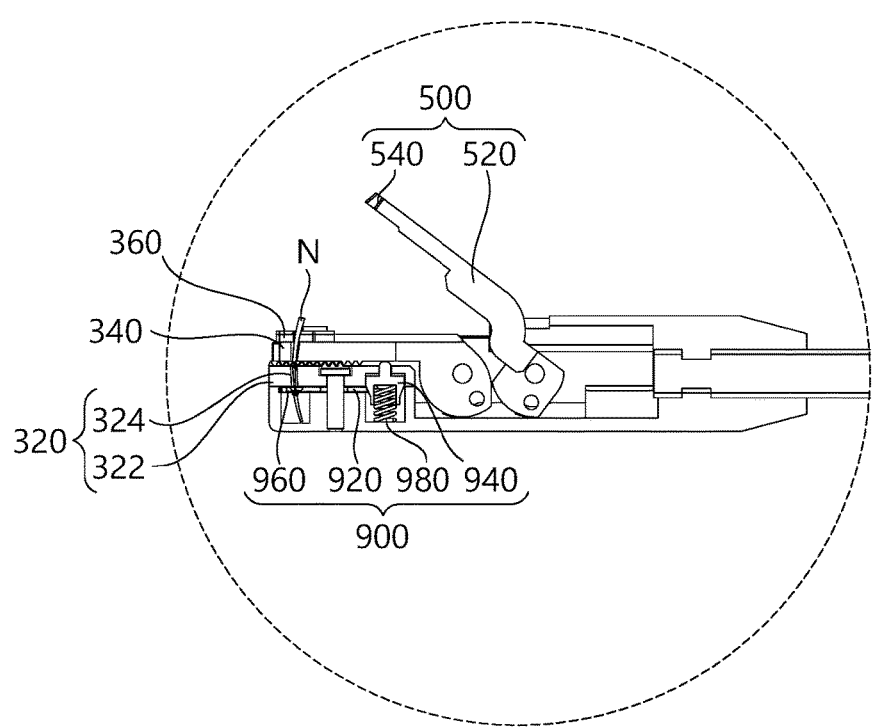
FIG. 6 is a cross-sectional view of the first mode of the suturing device for surgery illustrated in FIG. 5.
Figure 7:
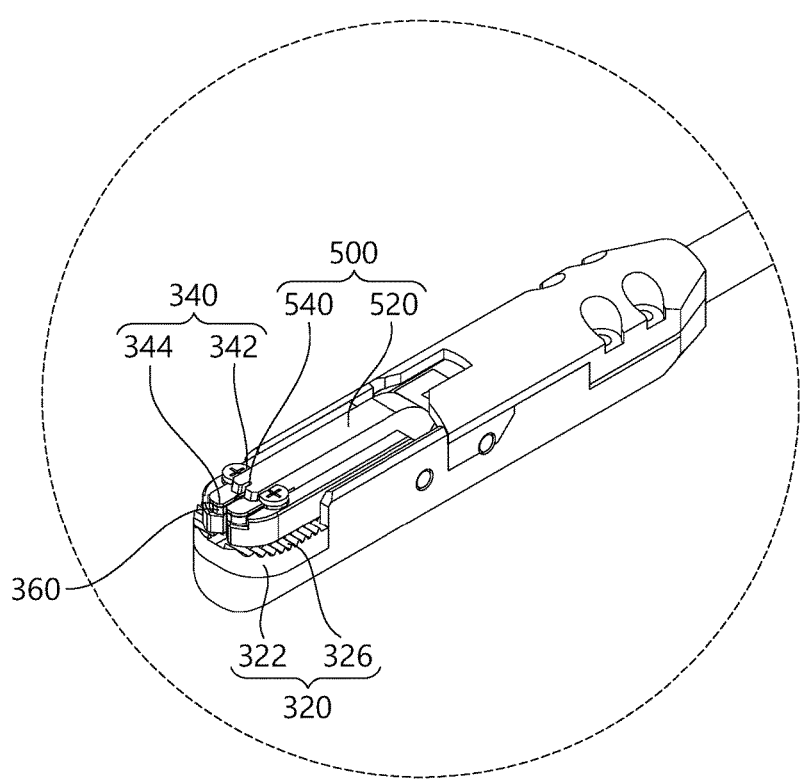
FIG. 7 is a second operational perspective view of a first mode of a suturing device for surgery according to an exemplary embodiment of the present invention.
Figure 8:
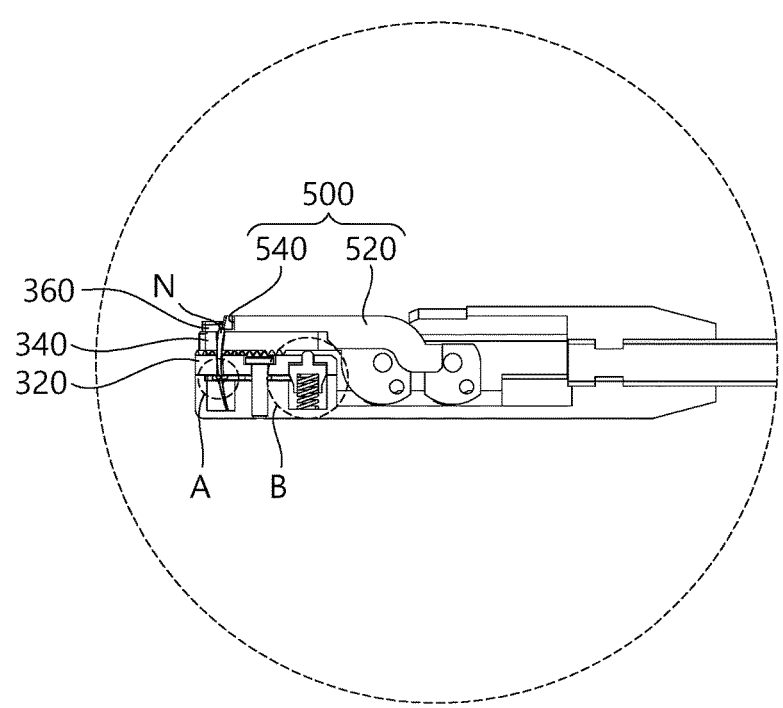
FIG. 8 is a cross-sectional view of the first mode of the suturing device for surgery illustrated in FIG. 7.
Figure 9:
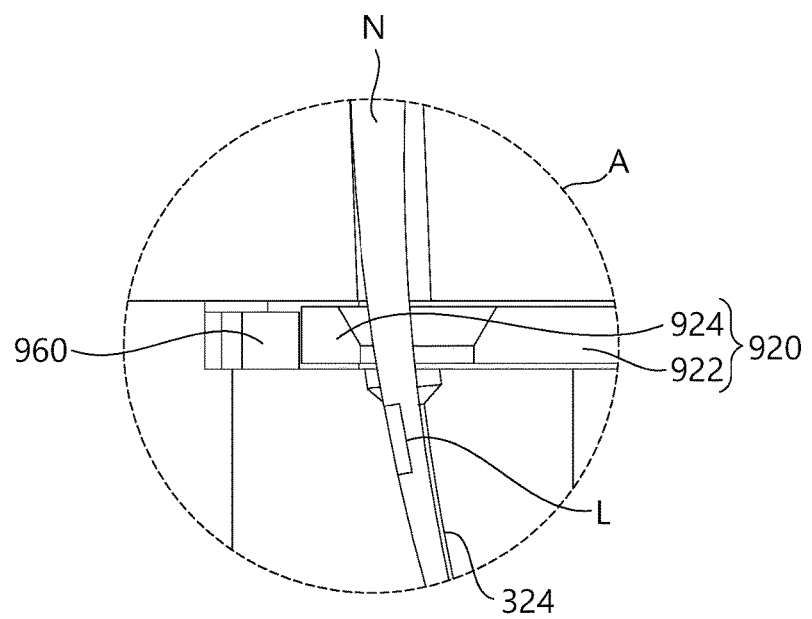
FIG. 9 is an enlarged view of area "A" illustrated in FIG. 8.
Figure 10:
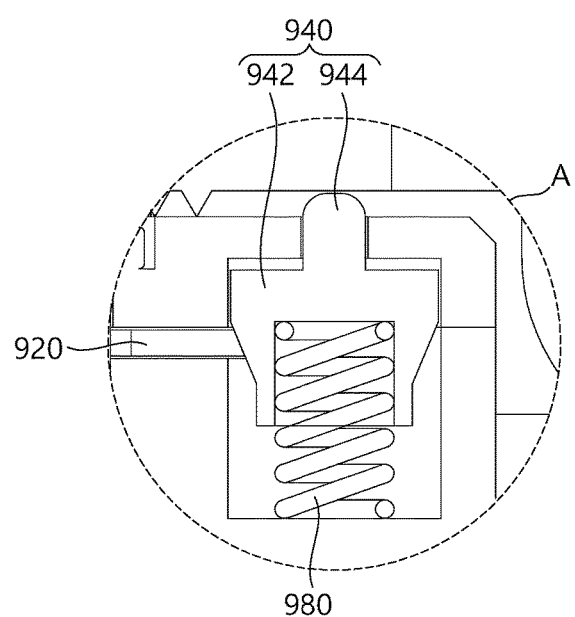
FIG. 10 is an enlarged view of area "B" illustrated in FIG. 8.
Figure 11:
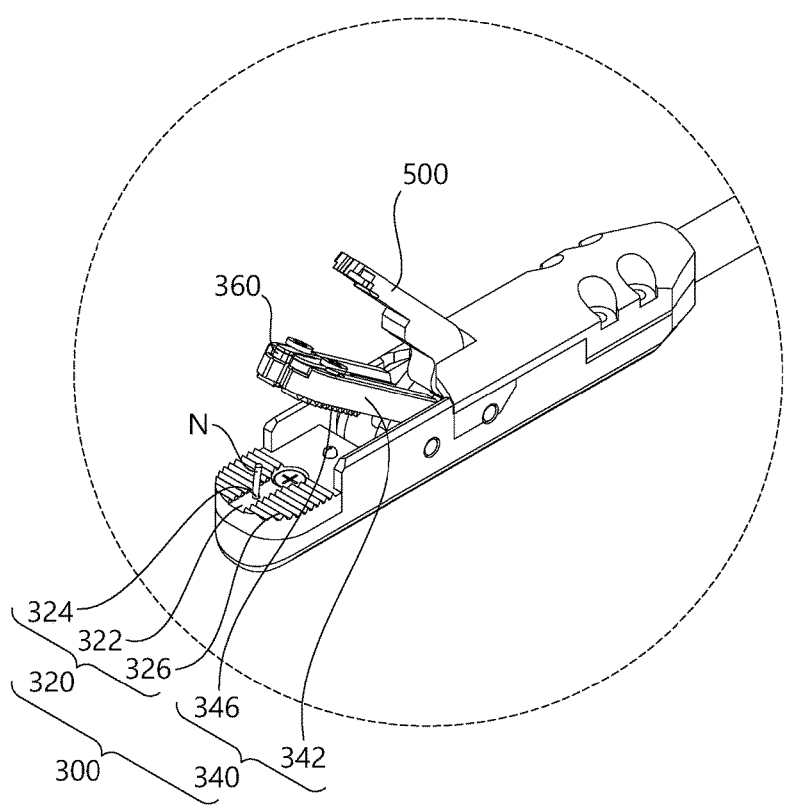
FIG. 11 is a third operational perspective view of a first mode of a suturing device for surgery according to an exemplary embodiment of the present invention.
Figure 12:
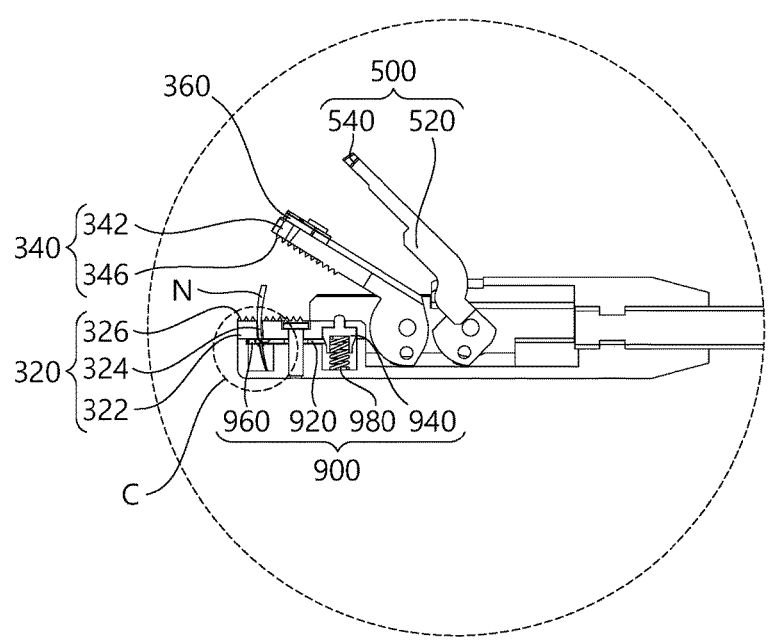
FIG. 12 is a cross-sectional view of the first mode of the suturing device for surgery illustrated in FIG. 11.
Figure 13:
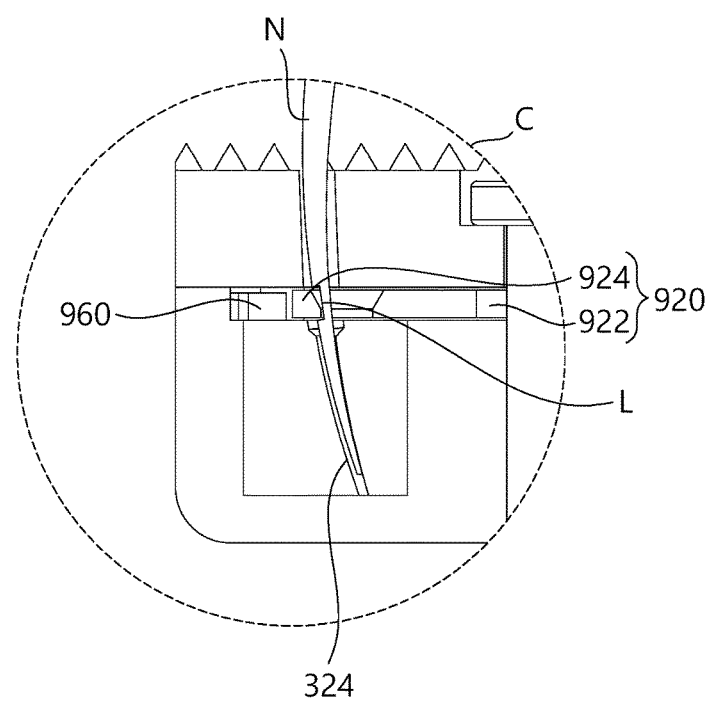
FIG. 13 is an enlarged view of area "C" illustrated in FIG. 12.
Figure 14:
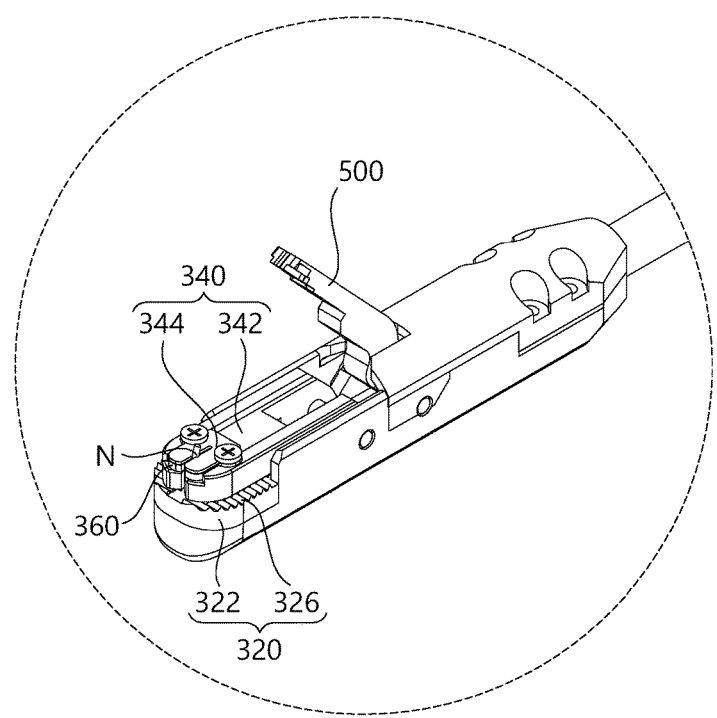
FIG. 14 is an operational perspective view of the second mode of the suturing device for surgery according to an exemplary embodiment of the present invention.
Figure 15:
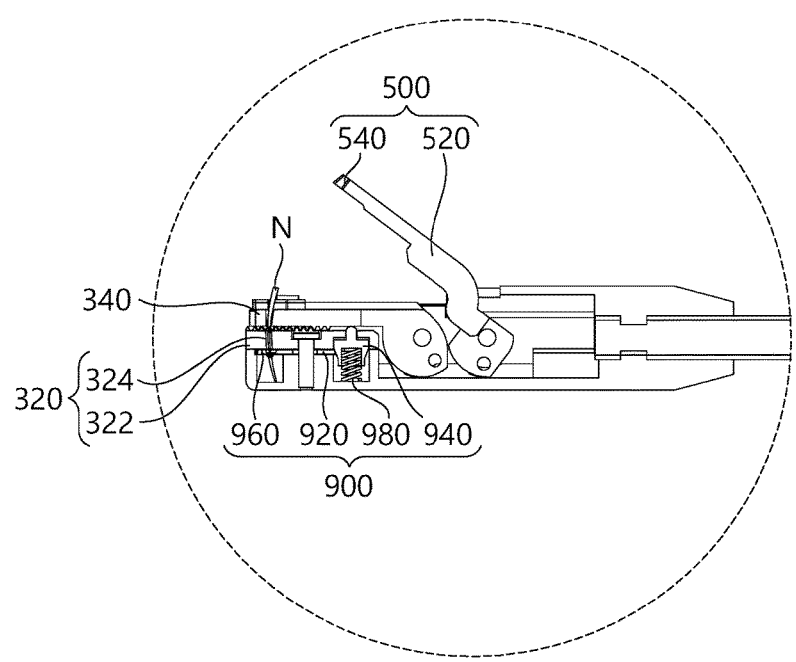
FIG. 15 is a cross-sectional view of the suturing device for surgery illustrated in FIG. 14 according to an exemplary embodiment of the present invention.

Then, FIG. 5 is a first operational perspective view of a first mode of the suturing device for surgery illustrated in FIG. 4; FIG. 6 is a cross-sectional view of the first mode of the suturing device for surgery illustrated in FIG. 5; FIG. 7 is a second operational perspective view of a first mode of a suturing device for surgery according to an exemplary embodiment of the present invention; FIG. 8 is a cross-sectional view of the first mode of the suturing device for surgery illustrated in FIG. 7; FIG. 9 is an enlarged view of area "A" illustrated in FIG. 8; FIG. 10 is an enlarged view of area "B" illustrated in FIG. 8; FIG. 11 is a third operational perspective view of a first mode of a suturing device for surgery according to an exemplary embodiment of the present invention; FIG. 12 is a cross-sectional view of the first mode of the suturing device for surgery illustrated in FIG. 11; FIG. 13 is an enlarged view of area "C" illustrated in FIG. 12; FIG. 14 is an operational perspective view of the second mode of the suturing device for surgery according to an exemplary embodiment of the present invention; FIG. 15 is a cross-sectional view of the suturing device for surgery illustrated in FIG. 14 according to an exemplary embodiment of the present invention; and HG. 16 is an enlarged view of area "D" illustrated in FIG. 15.

As illustrated in FIGS. 5 to 16, the suturing operation unit 300 is disposed on a front end, i.e., on a free end in a tube shape. The suturing operation unit 300 is provided as a pair of suturing operation units which are supported at a front end of the body unit 100 and are rotated between a first mode, in which the pair of suturing operation units are tooth-engaged to each other with a suture area (not shown) therebetween so that a suturing needle (N) supported by any one of the pair of suturing operation units passes through the suture area and is transferred to the other one of the pair of suturing operation units, and a second mode, in which the suturing needle (N) supported by the other one of the pair of suturing operation units in the first mode is transferred to any one of the pair of suturing operation units. As an exemplary embodiment of the present invention, the suturing operation unit 300 includes a suturing needle holder unit 320 and a suturing needle grip unit 340. Further, the suturing operation unit 300 further includes an elastic supporting unit 360.

The suturing needle holder unit 320 is supported at a front end of the body unit 100, and supports the suturing needle (N) transferred after passing through the suture area in the first mode. While the suturing needle holder unit 320 is fixed to a front end of the body unit 100 in the exemplary embodiments, the suturing needle holder unit 320 and the suturing needle grip unit 340 may rotate relative to each other. The suturing needle holder unit 320 of the present invention includes a holder body 322, a receiving hole 324, and a holder-engaging unit 326.

The holder body 322 forms the outer portion of the suturing needle holder unit 320, and is engaged with the grip body 342 of the suturing needle grip unit 340 which will be described later. The holder body 322 is engaged with the grip body 342 with the suture area therebetween in the first mode. The receiving hole 324 is formed on the holder body 322 and receives the suturing needle (N) in the first mode. That is, the suturing needle (N) passes through the suture area in the first mode to be received in the receiving hole 324. As described above, when the suturing needle (N) is received in the receiving hole 324 in the first mode, the suturing thread may pass through the suture area. The holder-engaging unit 326 is tooth-engaged with a grip-engaging unit 346 of the suturing needle grip unit 340 which will be described later. The holder-engaging unit 326 is tooth-engaged with the grip-engaging unit 346 with the suture area therebetween in the first mode, and holder-engaging unit 326 is directly tooth-engaged with the grip-engaging unit 346 in the second mode so that the suturing needle (N), received in the receiving hole 324, may be transferred to the suturing needle grip unit 340. More specifically, in the second mode, the holder-engaging unit 326 and the grip-engaging unit 346 are engaged without engaging the suture area.

The suturing needle grip unit 340 is engaged with or disengaged from the suturing needle holder unit 320. The suturing needle grip unit 340 transfers the suturing needle (N) gripped in the first mode to the suturing needle holder unit 320, and grips the suturing needle (N) held by the suturing needle holder 320 in the second mode. More specifically, the suturing needle grip unit 340 operates so that the suturing needle (N) gripped in the first mode may pass through the suture area to be transferred to the suturing needle holder unit 320 and to be held thereby; and the suturing needle grip unit 340 operates so that the suturing needle (N) held by the suturing needle holder unit 320 in the second mode may be gripped again. That is, by the rotation of the suturing needle grip unit 340 between the first mode and the second mode, continuous securing of the secure area may be performed. As an example of the present invention, the suturing needle grip unit 340 includes the grip body 342, the grip unit 344, and the grip-engaging unit 346.

The grip body 342 is provided to correspond to the aforementioned holder body 322. The grip body 342 rotates by the operation of a first driving unit 720 of the driving unit 700. For example, by using a driving force provided by the first driver 720, the grip body 342 is tooth-engaged with the holder body 322 of the suturing needle holder unit 320 with the suture area therebetween in the first mode; and the grip body 342 is directly tooth-engaged with the holder body 322 in the second mode. The grip unit 344 is releasably connected to the grip body 342 to correspond to the receiving hole 324 of the suturing needle holder unit 320 and to a cross-sectional area of the suturing needle (N). The grip unit 344 grips the suturing needle (N) so that the suturing needle (N) may pass through the suture area to be received in the receiving hole 324 of the suturing needle holder unit 320 in the first mode; and the grip unit 344 grips the suturing needle (N) after releasing the suturing needle (N) so that the suturing needle (N) may be received in the receiving hole 324. The grip unit 344 is required to grip the suturing needle (N) continuously during a suturing procedure. Accordingly, the grip unit 344 is releasably provided for the grip body 342 since there may be a high incidence of damage of the grip unit 344. Further, the grip unit 344 is releasably provided according to the cross-sectional area of the suturing needle (N). The grip-engaging unit 346 is provided to correspond to the holder-engaging unit 326. The grip-engaging unit 346 is similar to the holder-engaging unit 326, such that the detailed description thereof will be omitted.

The elastic supporting unit 360 is interposed between the grip body 342 and the grip unit 344 or is disposed on an upper portion of the grip body 344. As an example of the present invention, the elastic supporting unit 360 is interposed between the grip body 342 and the grip unit 344. The elastic supporting unit 360 is made of an elastic material, such as synthetic resin or synthetic rubber, which has elasticity. The elastic supporting unit 360 is elastically deformed according to the diameter of the gripped suturing needle (N) to elastically support the suturing needle (N).

The suturing needle pushing unit 500 applies pressure to the suturing needle (N) in the first mode to transfer the suturing needle (N) supported by any one of a pair of suturing operation units 300 to the other one of the pair of suturing operation units 300. As an example of the present invention, the suturing needle pushing unit 500 rotates at a position adjacent to the suturing needle grip unit 340. The suturing needle pushing unit 500 rotates by a driving force provided by a second driving unit 740 which will be described later. In the first mode, the suturing needle pushing unit 500 applies pressure to the suturing needle (N) so that the suturing needle (N), gripped by the suturing needle grip unit 340 in the first mode, may be inserted into the receiving hole of the suturing needle holder unit 320 to be held thereby. The suturing needle grip unit 340 includes a pushing body 520 and a through-hole 540.

The pushing body 520 rotates by a driving force provided by the second driving unit 740. In practice, the pushing body 520 rotates only in the first mode. The through-hole 540 is formed through the pushing body 520 at a position that corresponds to an upper portion of the suturing needle (N). The through-hole 540 is formed to allow the suturing thread, which is threaded through the suturing needle (N), to pass through. By having the through-hole 540, through which the suturing thread passes, the suturing thread may be prevented from being broken.

The driving unit 700 provides a driving force to at least any one of the pair of suturing operation units 300 so that the pair of suturing operation units 300 may rotate between the first mode and the second mode. Further, the driving unit 700 provides a driving force to the suturing needle pushing unit 500. The driving unit 700 includes the first driving unit 720 and the second driving unit 740, each of which provides a driving force independently from each other. Each of the first driving unit 720 and the second driving unit 740 includes a trigger, a connecting link or a wire, and the like. Although not illustrated herein, the first driving unit 720 and the second driving unit 740 may further include a motor in addition to a trigger, a connecting link or a wire, and the like.

The first driving unit 720 is connected to the suturing operation unit 300 to provide the suturing operation unit 300 with a driving force for rotation. In the exemplary embodiments of the present invention, the first driving unit 720 provides a driving force only to the suturing needle grip unit 340, but the first driving unit 720 is not limited thereto, and may be adapted to provide a driving force to the suturing needle holder unit 320 as well. The second driving unit 740 provides a driving force to the suturing needle grip unit 340. In practice, the second driving unit 740 provides a driving force to the suturing needle grip unit 340 only in the first mode. The first driving unit 720 and the second driving unit 740 operate differently in the first mode and the second mode.

More specifically, in the first mode, operation is performed in order of the first driving unit 720, the second driving unit 740, the first driving unit 720, and the second driving unit 700. Referring to the accompanying drawings, as illustrated in FIG. 4, the suturing needle grip unit 340 rotates by a driving force provided by the first driving unit 720, such that the suturing needle grip unit 340 may be engaged with the suturing needle holder unit 320 with the suture area therebetween to enable the suturing needle (N) to pass through the suture area. As illustrated in FIG. 6, the suturing needle pushing unit 500 rotates by a driving force provided by the second driving unit 740, such that the suturing needle pushing unit 500 may push the suturing needle (N) into the receiving hole 324 to be held thereby. Further, as illustrated in FIG. 11, by providing a driving force in order of the first driving unit 720 and the second driving unit 740, the suturing needle (N) is held by the suturing needle holder unit 320. In this case, the suturing needle (N) is locked by the operation of the locking unit 900 and is held by the suturing needle holder unit 320.

Figure 16:
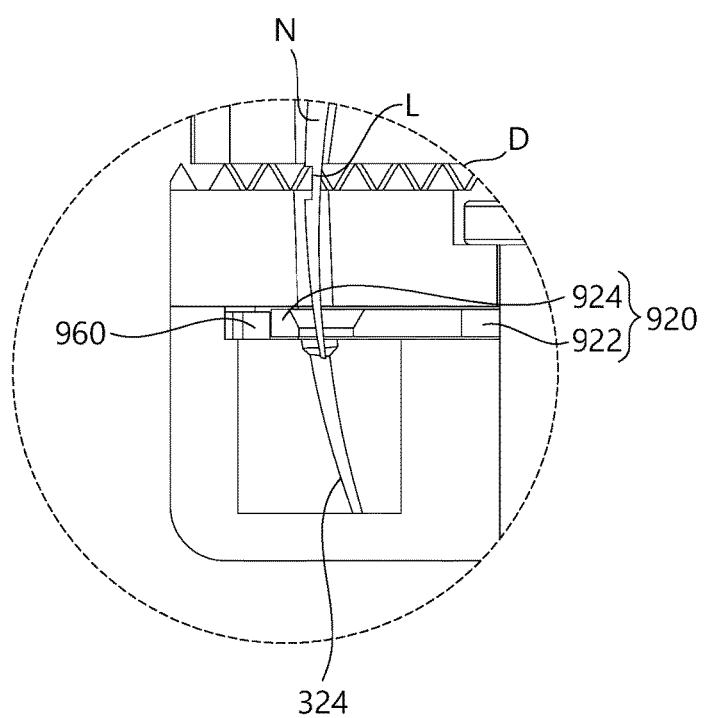
FIG. 16 is an enlarged view of area "D" illustrated in FIG. 15.

Referring to the drawings, as illustrated in FIGS. 14 to 16, a driving force provided by the first driving unit 700 is provided in the second mode so that the suturing needle (N) may be gripped by the suturing needle grip unit 340, and the grip is performed in the same manner as illustrated in FIG. 3. In this case, the locking unit 900 operates to unlock the locked suturing needle (N).

The locking unit 900 is disposed at any one of the pair of the suturing operation units 300, the one which is positioned at a downstream side in an insertion direction of the suturing needle (N), and locks and unlocks the suturing needle (N) between the first mode and the second mode. That is, in the first mode, the locking unit 900 locks the suturing needle (N) so that the suturing needle (N), after passing through the suture area, may be held by the suturing needle holder unit 320; and in the second mode, the locking unit 900 unlocks the suturing needle (N), held by the suturing needle holder unit 320, may be transferred to the suturing needle grip unit 340.

The locking unit 900 of the present invention includes a first locking unit 920, a second locking unit 940, a movement limiting unit 960, and an elastic member 980. The first locking unit 920 is disposed at a lower portion of the suturing needle holder unit 320, and reciprocates in a direction transverse to the insertion direction of the suturing needle (N), so as to be locked into and unlocked from the latch groove (L) of the suturing needle (N). The first locking unit 920 includes a first locking body 922 and a latch unit 924. The first locking body 922 reciprocates in a direction transverse to the insertion direction of the suturing needle (N). By using the second locking unit 940 and the movement limiting unit 960, the first locking body 922 reciprocates between a locking position illustrated in FIG. 13 and an unlocking position illustrated in FIG. 16. The latch unit 924 is formed to be engaged into the latch groove (L). The latch unit 924 is engaged into the latch groove (L) in the locking position to block the suturing needle (N) from moving.

The second locking unit 940 is disposed at one side of the first locking unit 920, and is lifted up and down by rotation of the suturing needle grip unit 340. The second locking unit 940 reciprocates between a locking position and an unlocking position of the suturing needle (N). More specifically, the second locking unit 940 provides a driving force to the first locking unit 920 in such a manner that the second locking unit 940 lifts up and down by making contact with and releasing contact from the suturing needle grip unit 340. The second locking unit 940 of the present invention includes a second locking body 942 and a button 944. The second locking body 942 comes into contact with one side of the first locking body 922. The one side of the first locking unit 920 comes into contact with the second locking unit 940 with a tapered shape or a round shape, and as the second locking unit 940 lifts up and down, the first locking unit 920 reciprocates in a direction transverse to the up-and-down direction of the second locking unit 940. More specifically, in the exemplary embodiments, the contacting area of the second locking body 942 and the first locking body 922 has a tapered shape, such that a force of up-and-down movement of the second locking body 942 is transformed into a force of reciprocal movement in a direction transverse to the movement direction of the second locking body 942. The button 944 is exposed to the outside of the suturing needle holder unit 320. The button 944 comes into contact with the suturing needle grip unit 340 when the suturing needle holder unit 320 is tooth-engaged with the suturing needle grip unit 340.

The movement limiting unit 960 is positioned adjacent to the other side of the first locking unit 920, which faces the one side of the first locking unit 920 that comes into contact with the second locking unit 940. The movement limiting unit 960 is positioned adjacent to the latch unit 924 of the first locking unit 920 to limit the movement of the first locking unit 920. Further, the movement limiting unit 960 is formed as a flat spring to provide elasticity to enable the latch unit 924 to be engaged into the latch groove (L) of the suturing needle (N). The elastic member 980 is disposed at a lower portion of the second locking unit 940 to elastically bias the second locking unit 940. More specifically, when pressure is applied by the suturing needle holder unit 320 to the second locking unit 940, the elastic member 980 provides elasticity so that the position of the second locking unit 940 may be restored.

In these configurations, the process of operating the suturing device 10 for surgery according to the exemplary embodiments of the present invention may be described as follows.

In the first mode, the suturing needle grip unit 340, which grips the suturing needle (N), and the suturing needle holder unit 320 are tooth-engaged with each other. A part of the suturing needle (N), gripped by the suturing needle grip unit 340, is inserted into the receiving hole 324 of the suturing needle holder unit 320. Then, by operating the suturing needle pushing unit 500, pressure is applied to the upper portion of the suturing needle (N). In this manner, the suturing needle (N) is inserted deeper into the receiving hole 324. Subsequently, a driving force is provided so that the suturing needle holder unit 320 and the suturing needle grip unit 340 may be spaced apart from each other, the second locking unit 940 is lifted up such that the first locking unit 920 is moved to enable the suturing needle (N) to be held by the suturing needle holder unit 320.

By contrast, in the second mode, the suturing needle (N), held by the suturing needle holder unit 320 during the first mode operation, is transferred again to the suturing needle grip unit 340. In this case, the second mode operation is performed to enable the suturing thread, after passing through the suture area in the first mode, to pass through the suture area again. The suture area may be sutured continuously by a series of repeated operations between the first mode and the second mode.

As described above, by providing the pair of suturing operation units that grips and holds the suturing needle, and by repeating a process of transferring the suturing needle from any one of the pair of suturing operation units to the other, the suture area may be sutured continuously, thereby improving efficiency in a suturing procedure.

Further, by repeating a process of transferring the suturing needle from any one the pair of suturing operation units to the other, a suturing procedure may be performed in a simple manner, thereby reducing an operator's fatigue.

While exemplary embodiments of the present invention have been described herein with reference to the accompanying drawings, it would be understood by those skilled in the art that various forms may be made without changing technical conception and essential features of the present invention. Accordingly, it should be understood that the aforementioned embodiments are illustrative in every aspect, and are not restrictive. The scope of the present invention is defined by the following claims rather than by the detailed description of the invention, and it should be construed that a meaning and a scope of the claim, and all changes or modified forms induced from an equivalent concept thereof are included in the scope of the present disclosure.

What is claimed is:

1. A suturing device for surgery, the device comprising:
a body unit; and
a pair of suturing operation units that are supported at a front end of the body unit and operate between a first mode, in which the pair of suturing operation units are tooth-engaged with each other with a suture area therebetween so that a suturing needle held by any one of the pair of suturing operation units passes through the suture area and is transferred to the other one of the pair of suturing operation units, and a second mode, in which the suturing needle held by the other one of the pair of suturing operation units in the first mode is transferred to any one of the pair of suturing operation units, the pair of suturing operation units comprising:
a suturing needle holder unit that is supported at the front end of the body unit and is configured to hold the suturing needle that is transferred after passing through the suture area in the first mode; and
a suturing needle grip unit that is engaged with or disengaged from the suturing needle holder unit, the suturing needle grip unit being configured to transfer the suturing needle gripped in the first mode to the suturing needle holder unit and configured to grip the suturing needle held by the suturing needle holder unit in the second mode,
wherein the suturing needle grip unit is configured to reciprocally rotate to be engaged with and disengaged from the suturing needle holder unit, and
wherein the suturing needle grip unit is engaged with the suturing needle holder unit with the suture area therebetween in the first mode, and is directly engaged with the suturing needle holder unit in the second mode; and
a driving unit configured to provide a driving force to at least any one of the pair of suturing operation units so that the pair of suturing operation units operate between the first mode and the second mode.

2. The suturing device of claim 1, further comprising a suturing needle pushing unit configured to apply pressure to the suturing needle in the first mode, so that the suturing needle, supported by any one of the pair of suturing operation units, is transferred to the other one of the pair of suturing operation units to be held thereby.

3. The suturing device of claim 2, wherein the suturing needle pushing unit has a through-hole through which a suturing thread, threaded through the suturing needle, passes.

4. The suturing device of claim 3, wherein the driving unit comprises:
a first driving unit configured to provide a driving force to at least any one of the pair of suturing operation units; and
a second driving unit configured to provide a rotational driving force to the suturing needle pushing unit.

5. The suturing device of claim 2, wherein the driving unit comprises:
- a first driving unit configured to provide a driving force to at least any one of the pair of suturing operation units; and
- a second driving unit configured to provide a rotational driving force to the suturing needle pushing unit.

6. The suturing device of claim 1, wherein the suturing needle holder unit is fixed to the front end of the body unit, and the suturing needle holder unit comprises a receiving hole into which the suturing needle is inserted.

7. The suturing device of claim 6, wherein the suturing needle grip unit comprises:
- a grip body that is configured to reciprocally rotate with respect to the suturing needle holder unit and is engaged with and disengaged from the suturing needle holder unit; and
- a grip unit that is releasably connected to the grip body to correspond to the receiving hole of the suturing needle holder unit and to a cross-sectional area of the suturing needle.

8. The suturing device of claim 7, wherein the pair of suturing operation units further comprises an elastic supporting unit that is interposed between the grip body and the grip unit or is disposed on an upper portion of the grip unit to elastically grip the suturing needle.

9. The suturing device of claim 1, wherein each of the suturing needle holder unit and the suturing needle grip unit is provided with an engaging unit that is engaged with respect to the suture area in the first mode to support the suture area.

10. The suturing device of claim 1, further comprising a locking unit that is disposed at any one of the pair of the suturing operation units, the one being positioned at a downstream side in an insertion direction of the suturing needle, and is configured to lock and unlock the suturing needle between the first mode and the second mode.

11. The suturing device of claim 10, wherein:
- the suturing needle has a latch groove; and
- the locking unit comprises:
  - a first locking unit that is disposed at a lower portion of the suturing needle holder unit and is configured to reciprocate in a direction transverse to the insertion direction of the suturing needle, so as to be locked into and unlocked from the latch groove of the suturing needle; and
  - a second locking unit that is disposed at one side of the first locking unit, and is lifted up and down by rotation of the suturing needle grip unit, to enable the first locking unit to reciprocate between a locking position and an unlocking position of the suturing needle.

12. The suturing device of claim 11, wherein the first locking unit has one side and an other side, and wherein the one side of the first locking unit comes into contact with the second locking unit with any one of a tapered shape or a round shape, and as the second locking unit lifts up and down, the first locking unit reciprocates in a direction transverse to the up-and-down direction of the second locking unit.

13. The suturing device of claim 12, wherein the locking unit further comprises a movement limiting unit, which is positioned adjacent to the other side of the first locking unit and faces the one side of the first locking unit, to limit movement of the first locking unit.

14. The suturing device of claim 11, wherein the locking unit further comprises a movement limiting unit that is positioned adjacent to the other side of the first locking unit that faces the one side of the first locking unit to limit movement of the first locking unit.

15. The suturing device of claim 14, further comprising an elastic member that is disposed at a lower portion of the second locking unit to elastically bias the second locking unit.

16. The suturing device of claim 1, wherein the suturing needle grip unit comprises:
- a grip body that reciprocally rotates with respect to the suturing needle holder unit and is engaged with and disengaged from the suturing needle holder unit; and
- a grip unit that is releasably connected to the grip body to correspond to a receiving hole of the suturing needle holder unit and to a cross-sectional area of the suturing needle.

* * * * *